US008252564B2

(12) United States Patent
Park et al.

(10) Patent No.: US 8,252,564 B2
(45) Date of Patent: Aug. 28, 2012

(54) *BURKHOLDERIA MULTIVORANS* STRAIN AND METHODS OF USING SAME

(75) Inventors: Oh-Jin Park, Daejeon (KR); Sang-Hyun Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 675 days.

(21) Appl. No.: 12/226,029

(22) PCT Filed: Apr. 5, 2007

(86) PCT No.: PCT/KR2007/001674
§ 371 (c)(1),
(2), (4) Date: Jan. 16, 2009

(87) PCT Pub. No.: WO2007/114668
PCT Pub. Date: Oct. 11, 2007

(65) Prior Publication Data

US 2011/0097768 A1 Apr. 28, 2011

(30) Foreign Application Priority Data

Apr. 6, 2006 (KR) ........................ 10-2006-0031323

(51) Int. Cl.
*C12P 13/02* (2006.01)

(52) U.S. Cl. ..................... 435/155; 435/252.1; 435/228; 435/280; 435/129

(58) Field of Classification Search ........................ None
See application file for complete search history.

(56) References Cited

U.S. PATENT DOCUMENTS

| | | | |
|---|---|---|---|
| 5,034,329 | A | 7/1991 | Cerbelaud et al. |
| 5,593,871 | A | 1/1997 | Anton et al. |
| 5,928,933 | A | 7/1999 | Dicosimo et al. |

FOREIGN PATENT DOCUMENTS

| | | |
|---|---|---|
| WO | WO 90/15146 | 12/1990 |

OTHER PUBLICATIONS

Chu et al. (Infection and Immunity, Oct. 2004, vol. 72, No. 10, pp. 6142-6147).*

Turton et al. (J. of Clinical Microbiology, Dec. 2003, vol. 41, No. 12, pp. 5750-5754).*

Jones et al. (Thorax, 2004, vol. 59, pp. 948-951).*

Fallon, R.D., et al., "A *Pseudomonas putida* capable of stereoselective hydrolysis of nitriles", Appl Microbiol Biotechnol (1997) 47: 156-161.

Martinkova, Ludmila et al., "Nitrile-and Amide-converting Microbial Enzymes: Stereo-, Regio- and Chemoselectivity", Biocatalysis and Biotransformation, 2002 vol. 20 (2), pp. 73-93.

Sonke, Theo, et al., "Aminoamidase-Catalyzed Preparation and Further Transformations of Enantiopure α-Hydrogen- and α,α-Disubstituted α-Amino Acids", pp. 23-58.

Hermes, H.F.M., et al., Purification and Characterization of an L-Aminopeptidase from *Pseudomonas putida* ATCC 12633, Applied and Environmental Microbiology, vol. 59, No. 12, Dec. 1993, pp. 4330-4334.

Ciskanik, Lawrence M., et al., Purification and Characterization of an Enantioselective Amidase from *Pseudomonas chlororaphis* B23, Applied and Environmental Microbiology, vol. 61, No. 3 Mar. 1995, pp. 998-1003.

NCBI Sequence Viewer v2.0, http://www.ncbi.nlm.nih.go/entrez/viewer.fcgi?tool=portal&db=protei . . . 2008.

* cited by examiner

*Primary Examiner* — Hope Robinson

(74) *Attorney, Agent, or Firm* — McKenna Long & Aldridge LLP

(57) ABSTRACT

The present invention relates to a novel *Burkholderia multivorans*, an amidase produced from the same, and a method for optical resolution of a racemic mixture using the same, and more particularly to a strain *Burkholderia multivorans* LG 31-3, an amidase having stereoselective substrate specificity, and a method for optical resolution of a racemic mixture using the same. The amidase produced from the novel *Burkholderia multivorans* LG 31-3 (KCTC 10920BP) according to the present invention can be useful to produce single enantiomer at a high optical purity since the racemic mixture may be easily optically resolved under enzyme reaction conditions of room temperature and normal pressure.

a b

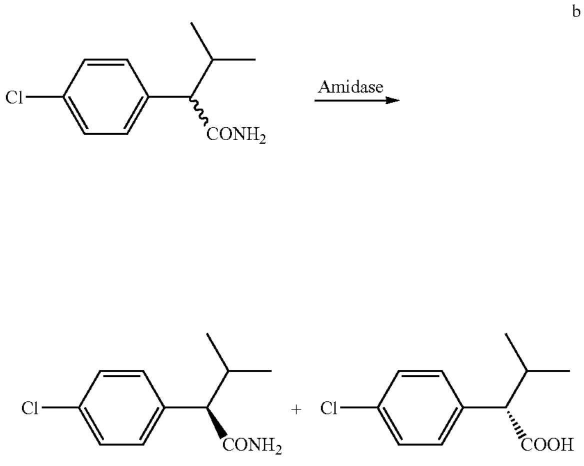

3 Claims, 6 Drawing Sheets

2: molecular markers
3 ~ 7: IEC fractions 2 molecular markers
3-5: GFC fractions 2: molecular markers
3: Band 2
4: Band 3
5: Band 4

SEQUENCE LISTING

```
<160> NUMBER OF SEQ ID NOS: 2

<210> SEQ ID NO 1
<211> LENGTH: 19
<212> TYPE: PRT
<213> ORGANISM: Burkholderia sp.
<220> FEATURE:

<400> SEQUENCE: 1

Thr Thr Leu Gly Ser Leu Thr Leu Thr Glu Ala Arg His Ala Leu Arg
  1               5                  10                  15

Arg Glu Phe


<210> SEQ ID NO 2
<211> LENGTH: 29
<212> TYPE: PRT
<213> ORGANISM: Burkholderia sp.
<220> FEATURE:

<400> SEQUENCE: 2

Val Thr Arg Pro Val Arg Leu Ala Leu Pro Arg Thr Thr Phe Trp Arg
  1               5                  10                  15

Gly Leu Ala Ala Asp Val Asp Ala Leu Ala Gln Gln Ala
             20                  25
```

*BURKHOLDERIA MULTIVORANS* STRAIN AND METHODS OF USING SAME

This application is an application based on International Patent Application No. PCT/KR2007/001674 filed Apr. 5, 2007, which claims the benefit of Korean Application No. 10-2006-0031323 filed Apr. 6, 2006, which are hereby incorporated by reference for all purposes as if fully set forth herein.

TECHNICAL FIELD

The present invention relates to a novel *Burkholderia multivorans*, an amidase produced from the same, and a method for optical resolution of a racemic mixture using the same, and more particularly to a strain *Burkholderia multivorans* LG 31-3, an amidase having stereoselective substrate specificity, and a method for optical resolution of a racemic mixture using the same.

BACKGROUND ART

More complicated Compounds have been developed in the field of pharmacology and agricultural chemistry, and there have been an increasing number of compounds having more than one asymmetric carbon. There are commercially available compounds that have been on the market as a racemic mixture. In many cases, it has been reported that only one optically active compound in the racemic mixture exhibits biological activities, and the other compounds exhibit no biological activity, or are harmful to mammalians or environments. Accordingly, it is necessary to develop biological and/or chemical techniques that can synthesize a desired single isomer. As the biological and/or chemical techniques that can synthesize only one optically active compound, an asymmetric synthesis, a method for concentrating an enantiomer, or stereospecific synthesis of an organic compound using enzymes, etc. have been recently studied all over the world, and, among them, many studies on the optical resolution of a racemic mixture using amidase has been reported.

Esfenvalerate [(S)-α-cyano-3-phenoxybenzyl (S)-2-(4-chlorophenyl)-3-methylbutyrate] whose much attention has been recently attracted in the racemic mixture is a chiral isomer of racemic fenvalerate, a biological activity of which results mainly from (S)-isomers (FIG. 1*a*).

(S)-2-(4-chlorophenyl)-3-methylbutyric acid used for the synthesis of esfenvalerate may be synthesized using various methods. As one of the methods for producing an optically active compound (R)— or (S)—(S)-2-(4-chlorophenyl)-3-methylbutyric acid, there is an optical resolution technique in which optically pure amine (for example, (R)- or (S)-phenylethylamine) as a resolving agent is added to a racemic mixture and a desired compound is separated from the racemic mixture. However, the problem is that the resolving agent is very expensive and its process is complicated.

Also, as one of the methods for synthesizing (S)-2-(4-chlorophenyl)-3-methylbutyric acid, there is a method employing lipase or esterase by using ester as a starting material, or a method employing nitrile hydratase having stereoisomeric selectivity (Fallon et al., *Appl. Microbiol. Biotechnol.* 47: 156, 1997).

Meanwhile, in order to optically resolve a certain racemic mixture, methods for selectively hydrolyzing an enantiomer using an enzyme such as esterase, amidase (lipase) and protease has been known. For example, a method for hydrolyzing a *Candida rugosa*-derived lipase using racemic methyl-2-chloropropionate(Methyl-2-chloropropionate) has been known (Dahod & Siuta-Mangano, *Biotech. Bioeng.*, 30:995, 1987). Also, a method for synthesizing (R)-2-(4-hydroxyphenoxy)propionic acid using a purified *Candida rugosa*-derived amidase has been reported (WO 1990/15146).

It is very effective to use an enzyme for the optical resolution of a racemic mixture, but it is not only very difficult to confirm which racemic compounds are optically resolved with enzyme, but also to confirm which enzymes are particularly effective to resolve racemic compounds. For example, U.S. Pat. No. 5,928,933 discloses that, in order to optically resolve racemic 4-oxo-1,2-pyrrolidinedicarboxylic acid dialkyl ester, 44 enzymes selected from proteases, amidases and esterases was tested for specificity of enzyme activity, and one of the 44 enzymes shows an optical purity of 95%. As described above, it is very important to find suitable combinations of enzymes with substrates through continuous studies since the selectivity and optical purity (% ee) of isomers are varied according to the kinds of the used enzymes and the chemical structure of the substrate, etc.

Meanwhile, in the case of the racemic (R),(S)-2-(4-chlorophenyl)-3-methylbutyramide which is the subject for the optical resolution in the present invention, it is yet not known that the racemic mixture is optically resolved using amidase. The conventional optical resolution using enzymes is mainly limited to the synthesis of an intermediate, aryloxypropionic acid, of a prop-based herbicide, the synthesis of an intermediate, arylpropionic acid, of a profen-based antiinflammatory agent, etc., but there is no precedent for using enzymes for the optical resolution of (R),(S)-2-(4-chlorophenyl)-3-methylbutyramide.

Meanwhile, the amidase, which hydrolyzes carboxylic acid amide, belongs to Enzyme Class E.C.3.4. It has been known that the amidase, reported until now, is extensively present in the microorganism such as *Corynebacterium, Pseudomonas, Bacillus, Brevibacterium, Rhodococcus, Alcaligenes*, etc. It has been known that the amidases are mainly induced and expressed to exhibit specific substrate specificities in every microorganism (Martinkova & Kren, *Biocat. Biotrans.*, 20:73, 2002). In particular, *Pseudomonas putida* ATCC 12633-derived amidase is used in the method used by DSM (the Netherlands), which is a method for synthesizing D-amino acid or L-amino acid using D,L-amino acid amide (Sonke et al., *Stereoselective Biocatalysis*, p 23-58, 2000, Patel, R. N. ed., Marcel Dekker). For example, the *Pseudomonas putida* ATCC 12633-derived amidase has been reported as a useful enzyme that stereoselectively hydrolyze L-phenylglycinamide into D-phenylglycinamide and L-phenylglycine (Hermes et al., *Appl. Environ. Microbiol.*, 59:4330, 1993). However, its substrate specificity is not completely characterized, and there is a need for a novel amidase which may be produced more economically and react with substrates that are not converted by the conventional amidase.

Accordingly, there are urgent needs for screening and developing a novel amidase capable of being used for the optical resolution, a novel strain capable of producing the amidase, and a method for optically resolving a racemic mixture using the novel strain in the art.

DISCLOSURE OF INVENTION

Accordingly, the inventors have ardent attempts to develop a novel strain capable of producing an enzyme which may be used for the optical resolution. As a result, the inventors screened a strain *Burkholderia multivorans* LG 31-3 from a various kinds of microorganisms collected from soils, watercourses, and various wastewaters in the broad regions, to find a strain producing an amidase that stereoselectively hydrolyze a certain racemic compound, and then they found that the strain produces an amidase that selectively hydrolyze (S)-stereoisomer. Therefore, the present invention was completed, based on the above-mentioned facts.

Accordingly, the present invention is designed to solve the problems of the prior art, and therefore it is an object of the present invention to provide a strain *Burkholderia multivorans* LG 31-3 (KCTC 10920BP) having an ability to produce amidase.

It is another object of the present invention to provide a method for producing amidase, the method including a step of culturing the strain *Burkholderia multivorans*, and an amidase having stereoselective substrate specificity.

It is still another object of the present invention to provide a method for optical resolution of a racemic mixture, the method including a step of treating a racemic mixture in the presence of the strain *Burkholderia multivorans*, a cell lysate of the strain or the amidase as defined in claim 4.

In order to accomplish the above objects, the present invention provides a strain *Burkholderia multivorans* having an ability to produce amidase.

In the present invention, the strain may be *Burkholderia multivorans* LG 31-3 (KCTC 10920BP).

Also, the present invention provides a method for producing an amidase, the method including steps of culturing the strain *Burkholderia multivorans*; and recovering amidase from the cultured strain.

Also, the present invention provides an amidase produced according to the above method, which has an N-terminal amino acid sequence set forth in SEQ ID NO: 1 and stereoselective substrate specificity.

The present invention provides an amidase having an internal amino acid sequence set forth in SEQ ID NO: 2.

Also, the present invention provides a method for optical resolution of a racemic mixture, the method including steps of treating a racemic mixture in the presence of the strain *Burkholderia multivorans*, a cell lysate of the strain or the amidase as defined in claim 4.

In the present invention, the racemic mixture is racemic (R),(S)-2-(4-chlorophenyl)-3-methylbutyramide represented by the following Formula 1.

Formula 1

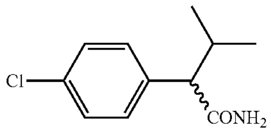

Also, the present invention provides a method for producing (S)-2-(4-chlorophenyl)-3-methylbutyric acid, the method including a step of optically resolving racemic (R),(S)-2-(4-chlorophenyl)-3-methylbutyramide, represented by the Formula 1, in the presence of the strain *Burkholderia multivorans*, a cell lysate of the strain or the amidase.

BRIEF DESCRIPTION OF THE DRAWINGS

FIGS. 3*a* and 3*b* show electrophoretic results of fractions on SDS-PAGE after ion exchange chromatography (IEC) and gel filtration chromatography (GFC), and FIG. 3*c* shows that native gel electrophoresis is performed since pure proteins are not obtained even after the GFC.

BEST MODES FOR CARRYING OUT THE INVENTION

Figure 1A:
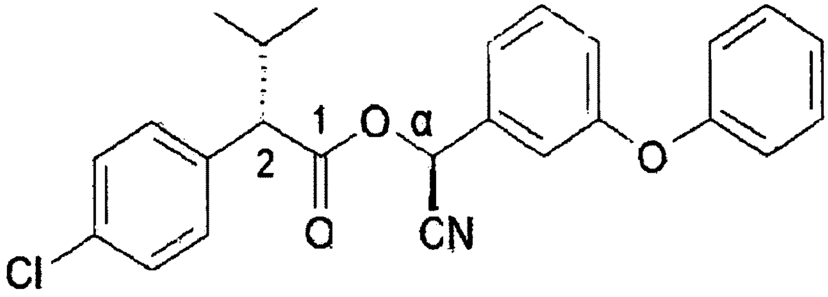
FIG. 1*a* is a chemical formula showing esfenvalerate [(S)-α-cyano-3-phenoxybenzyl(S)-2-(4-chlorophenyl)-3-methylbutyrate]

Hereinafter, preferred embodiments of the present invention will be described in detail.

In order to obtain a microorganism producing amidase which has a stereoselective substrate specificity and can be used for an optical resolution of a racemic mixture, the inventors screened various kinds of pure strains from farm soils all over the country, soils around the industrial complexes, waste water in the wastewater treatment plants, etc., and performing repeated experiments on these strains and other privately-owned strains several times.

These strains were incubated at 30° C. in minimal liquid media containing a compound ((R),(S)-2-(4-chlorophenyl)-3-methylbutyramide, fenvaleramide, FAA) of Formula 1 as a nitrogen source, and then a test tube solution in which each of the strains is growing was incubated in a minimal solid medium containing FAA. Colonies grown in the media were judged to decompose the FAA, and then purely cultured again to select colonies in which the starting materials have a conversion ratio of 50% to the time on HPLC (a conversion ratio of 50% in selectivity of 100%), thereby to purify strains producing amidase.

The strains obtained according to the above-mentioned method were cultured by shaking in a complex liquid medium (medium D) containing FAA as an inducing agent, centrifuged and re-suspended in a phosphate buffer. Some of the suspension was mixed in a racemic (R), (S)-2-(4-chlorophenyl)-3-methylbutyramide reaction solution, reacted at 30° C., and the resultant reaction products were analyzed on HPLC (C-18 Optimapak, RStech) to confirm hydrolytic ability on (R),(S)—N-(2,6-dimethylphenyl) alanine methyl ester. In order to select strains that produce amidase having a stereoselective hydrolytic ability among approximately 50 strains having a confirmed hydrolytic ability, the 50 strains were analyzed with Chiral-HPLC [column: Chiral AGP ChromTech (Congleton, UK), solvent: $Na_2HPO_4$ aqueous solution (10 mM pH 6.0)/ethanol=95/5 vol %, flow rate: 0.9 ml/min, 230 nm, (S)-acid 8.0 min, (R)-acid 6.0 min, (S)-amide 20 min, (R)-amide 16 min] to separate strains having a stereoselective hydrolytic ability on the compound (R),(S)-2-(4-chlorophenyl)-3-methylbutyramide.

Among the separated strains, 10 strains including the strain LG 31-3 having an excellent stereoselective hydrolytic ability (conversion ratio>35%, S/R selectivity>60/1) were selected and characterized. A gram-negative 96-well microplate (Biolog) coated with 95 carbon sources was used to identify the strain LG 31-3 (39% conversion ratio, S/R selectivity 99/1) having the most excellent stereoselectivity using a fingerprinting analysis (Biolog). The fingerprinting analysis is a method utilizing the principle of oxidizing a carbon source in a 96-well microplate while inoculated stains breathe and reducing a tetrazolium dye in the 96 wells to aim to have a violet color.

The previously cultured isolated strain suspension was inoculated in the 96-well microplate and cultured, and the isolated strains were then measured for abilities to utilize and oxide substrates as 95 carbon sources. The obtained results were applied to a Biolog identification program to identify the strains. As a result, the strain of the present invention was identified as *Burkholderia multivorans* sp. (Table 3). The resultant strain was named "*Burkholderia multivorans* LG 31-3", and deposited in KCTC (Korean Collection for Type Cultures) of KRIBB (Korea Research Institute of Bioscience and Biotechnology) on Mar. 13, 2006. The Deposition number was "KCTC 10920BP." The deposition was made under the Budapest Treaty in KRIBB and is available to the public. The address of KRIBB is 125 Gwahak-ro Yuseong-gu, Daejeon, 306-809, Republic of Korea.

Racemic (R),(S)-2-(4-chlorophenyl)-3-methylbutyramide was reacted with the whole cell and crude enzyme solution prepared according to the above-mentioned method, and analyzed at a conversion ratio of 50% or less using HPLC and GC to determine its stereoselectivity. Activity of the amidase according to the present invention was measured in the precipitate fraction at an increasing concentration of ammonium sulfate ($(NH_4)_2SO_4$) from 0 to 60 Volume %.

The present invention provides an amidase including an N-terminal amino acid sequence (SEQ ID NO: 1) and an internal amino acid sequence (SEQ ID NO: 2. A DNA gene of the amidase was isolated by closely analyzing amino acid sequences of the previously known amidases, designing primer sequences based on the conserved regions of the known amidases and amplifying a fragment using PCR (polymerase chain reaction). The amidase may be produced in the strain, but may be produced in a host system such as *Escherichia coli*, yeasts, *Bacillus* sp., etc. in the form of a recombinant protein, a gene of which contains an amidase gene. Also, the amidase may be used as a free enzyme, or used in the form of being fixed on a certain carrier or in the form of CLEC (cross-linked enzyme crystals) and CLEA (cross-linked enzyme aggregates).

It is expected that the amidase produced in the strain may be selectively used for an optical resolution of other racemic mixtures in addition to the compound (R),(S)-2-(4-chlorophenyl)-3-methylbutyramide, the context of which should be also defined without departing from the scope of the present invention.

Figure 1B:
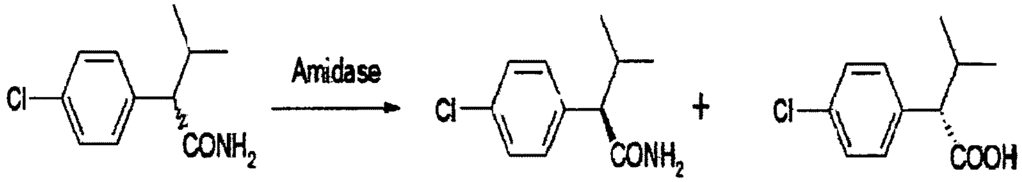
FIG. 1*b* is a scheme showing hydrolysis of (R),(S)-2-(4-chlorophenyl)-3-methylbutyramide using amidase produced in the LG 31-3 strain according to the present invention.

It was confirmed that the amidase produced by the novel strain has a stereoselective substrate specificity to certain racemic compounds in the racemic mixture. According to the experiment carried out by the inventors, the amidase may be optically resolved for the racemic (R),(S)-2-(4-chlorophenyl)-3-methylbutyramide represented by Formula 1. That is to say, the amidase selectively hydrolyze only one compound (S)-2-(4-chlorophenyl)-3-methylbutyramide in the racemic (R),(S)-2-(4-chlorophenyl)-3-methylbutyramide under reaction conditions of room temperature and normal pressure to yield (S)-2-(4-chlorophenyl)-3-methylbutyric acid (FIG. 1*b*). The compound (S)-2-(4-chlorophenyl)-3-methylbutyric acid prepared thus may react with (S)-α-cyano-3-phenoxybenzyl alcohol to yield esfenvalerate having a biochemical activity (FIG. 1*a*). Description of the esterification reaction is omitted since the esterification reaction is known to those skilled in the art.

Hereinafter, preferred embodiments of the present invention will be described in detail referring to the accompanying drawings. However, the description proposed herein is just a preferable example for the purpose of illustrations only, not intended to limit the scope of the invention, so it should be understood that other equivalents and modifications could be made thereto without departing from the spirit and scope of the invention.

In particular, it is described that the amidase produced from the strain *Burkholderia multivorans* sp. LG 31-3 (KCTC 10920BP) is used in the following Examples to easily perform an optical resolution on the racemic (R), (S)-2-(4-chlorophenyl)-3-methylbutyramide, thereby to yield a single enantiomer (S)-2-(4-chlorophenyl)-3-methylbutyric acid at a high optical purity, but it will also be apparent to those skilled in art that the amidase produced in the strain may be selectively used for the optical resolution of other racemic mixtures in addition to the optical resolution of the racemic (R), (S)-2-(4-chlorophenyl)-3-methylbutyramide.

Example 1

Screening of Amidase-Producing Strain

Test samples from farm soils all over the country, soils around the industrial complexes, waste water in the wastewater treatment plants, etc. were diluted with a sterile solution (0.1M potassium phosphate buffer pH 7.2) to prepare a minimal SFAA medium (FAA 2 g, glucose 2 g, $K_2HPO_4$ 7 g, $KH_2PO4$ 3 g, $MgSO_4$-$7H_2O$ 0.1 g, sodium citrate 0.5 g, vitamin solution 10 ml, trace element solution 5 ml/l, pH 7.0; see Table 1) containing a compound FAA (fenvaleramide) of Formula 1 as a sole nitrogen source.

The resultant medium was autoclaved at 121° C. for 15 minutes, and the vitamin solution, the trace element solution and $MgSO_4$-$7H_2O$ were respectively filtered and added to the medium. Test tubes containing the medium were inoculated with the waste waters diluted with a sterile solution and cultured at 35° C. at 200 rpm, and then their turbidities were observed with the naked eye. The test tubes in which microorganisms grow were selected, and the selected culture solutions were plated on solid media obtained by adding 1.5% agar to an SFAA liquid medium, and then stationarily cultured at 35° C. to obtain about 200 strains forming a colony.

TABLE 1

| Trace Element Solution | | Vitamin Solution | |
|---|---|---|---|
| Components | Content (/L) | Components | Content (/L) |
| $Na_2B_4O_7$•$10H_2O$ | 100 mg | Thiamin•HCl | 4 mg |
| $CoCl_2$•$6H_2O$ | 20 mg | Riboflabin | 2 mg |
| $CuSO_4$•6H2O | 10 mg | Pentothecic acid | 4 mg |
| NiCl•$H_2O$ | 10 mg | Pyridoxin•HCl | 4 mg |
| $Na_2MoO_4$•$2H_2O$ | 10 mg | p-aminobenzoicc acid | 4 mg |
| CaCl•2H20 | 10 mg | Nicotinic acid | 4 mg |
| $MnSO_4$•$5H_2O$ | 100 mg | Inositol | 20 mg |
| $FeSO_4$•$7H_2O$ | 200 mg | Biotin (0.02% sol) | 100 μl |

Example 2

Production of Amidase and Reaction of Whole Cell

Among the amidase-producing strains isolated in Example 1, 200 ml of single colonies from stock solutions of strains SFAA 9-4, MC 12-1 (media C 12-1), SFAA 12-5, SFAA 31-1, LG 31-3 and A118-2 were inoculated in complex media D ($K_2HPO_4$ 10 g, $NaH_2PO_4$ 5 g, NaCl 0.5 g, $CaCl_2$-$2H_2O$ 0.02 g, $(NH_4)_2SO_4$ 3.5 g, yeast extract 0.5 g, $MgSO_4$-$7H_2O$ 0.3 g, glucose 4 g, trace element solution 10 ml/l, pH 7.5) containing 2 g/l FAA, cultured at 30° C. for 24 hours, and then centrifuged to separate a supernatant and a cell pellet, and the cell pellet was suspended in 25 ml of a 0.1M Tris-HCl solution (pH 8.0). 3 ml of the cell suspension and 30 μl of the FAA reaction solution (methanol at a concentration of 211.2 mg/2 ml) was mixed, and the resultant mixture was tested for reactivity using a resting cell biotransformation.

The resulting (R),(S)-2-(4-chlorophenyl)-3-methylbutyric acid and the reactant (R),(S)-2-(4-chlorophenyl)-3-methylbutyramide were analyzed for the conversion ratio through RP-HPLC analysis (acetonitrile/water=7/3) and the S/R selectivity through Chiral-HPLC. The results are listed in the following Table 2. Table 2 illustrate the FAA conversion ratio and the selectivity using a resting cell HPLC Analysis Condition Analysis by Chiral-HPLC [column: Chiral AGP ChromTech (Congleton, UK), solvent: $Na_2HPO_4$ aqueous solution (10 mM pH 6.0)/ethanol=95/5 vol %, flow rate: 0.9 ml/min, 230 nm, (S)-acid 8.0 min, (R)-acid 6.0 min, (S)-amide 20 min, (R)-amide 16 min]

TABLE 2

| Strains | SFAA 9-4 | MC 12-1 | SFAA 12-5 | SFAA 31-1 | LG 31-3 | A118-2 |
|---|---|---|---|---|---|---|
| Conversion Ratio (%) | 41 | 39 | 36 | 35 | 39 | 31 |
| S/R Selectivity (* $ee_p$) | 97.9 | 97.9 | 97.8 | 97.5 | 98.0 | 96.7 |

(* $ee_p$) = {[(S)-2-(4-chlorophenyl)-3-methylbutyric acid-(R)-2-(4-chlorophenyl)-3-methylbutyric acid]/[(S)-2-(4-chlorophenyl)-3-methylbutyric acid + (R)-2-(4-chlorophenyl)-3-methylbutyric acid]}

Also, the resting cell biotransformation on the racemic (R),(S)-MAP was performed in the same manner as described above. As listed in Table 2, the LG 31-3 strain had an S/R selectivity of 98.0% $ee_p$ at a conversion ratio of 39% from (R),(S)-2-(4-chlorophenyl)-3-methylbutyramide to (S)-2-(4-chlorophenyl)-3-methylbutyric acid. From this fact, it was confirmed that the LG 31-3 strain produces an amidase that selectively hydrolyzes (S)-2-(4-chlorophenyl)-3-methylbutyramide in the racemic (R),(S)-2-(4-chlorophenyl)-3-methylbutyramide to produce (S)-2-(4-chlorophenyl)-3-methylbutyric acid. FIG. 1*b* is a scheme showing hydrolysis of (R),(S)-2-(4-chlorophenyl)-3-methylbutyramide using amidase produced in the LG 31-3 strain according to the present invention.

Example 3

Identification of Strain

For the LG 31-3 strain that produces an amidase having stereoselective substrate specificity in Example 2, the amidase was measured for the utilization of substrate on a gram-negative 96-well plate coated with 95 carbon sources (Biolog) (Table 3). The results by the fingerprinting analysis are listed in the following Table 3.

TABLE 3

Biolog GN(Registration No. 376)

| | | | | | | |
|---|---|---|---|---|---|---|
| − water | − α-cyclodextrin | − dextrin | − glycoger | + tween 40 | + tween 80 | − N-acetyl-D-galactosamine |
| − i-erythritol | + D-fructose | + L-fucose | + D-galactose | − gentiobiose | + α-D-glucose | + m-inositol |
| − D-melibiose | β-methyl-D glucoside | − D-psicose | − D-raffinose | − L-rhamnose | + D-sorbitol | − sucrose |
| − acetic acid | + cis-aconitic acid | + citric acid | v fomic acid | v D-galactonic acid lactone | + D-galacturonic acid | + D-gluconic acid |
| v p-hydroxy phenylacetic acid | − itaconic acid | v α-keto butyric acid | − α-keto glutaric acid | − α-keto valeric acid | − D,L-lactic acid | + malonic acid |
| + bromo succinic acid | − succinamic acid | − glucuronamide | − alaninamide | + D-alanine | + L-alanine | + L-alanyl-glycine |
| + L-histidine | + hydroxy L-proline | − L-lencine | − L-crnithine | + L-pheylalanine | + L-proline | + L-pyroglutamic acid |
| − urocanic acid | − inosine | − uridine | − thymidine | + phenyl ethylamine | − putrescine | + 2-amino ethanol |

| | | | | |
|---|---|---|---|---|
| + N-acetyl-D-glucosamine | + adonitol | − L-arabinose | + D-arabitol | − cellobiose |
| − α-D-lactose | − lactulose | − maltose | + mannitol | + D-amanose |
| − D-trehalose | − turanose | + xylitol | + methyl pyruvate | + mono-methyl succinate |
| + D-glucosamini acid | + D-glucuronic acid | v α-hydroxy-butyric acid | − β-hydroxy-butyric acid | − γ-hydroxy-butyric acid |
| + propioic acid | + quinic acid | + D-saccharicenyl acid | + sebacicc acid | + succinic acid |
| + L-asparagine | − L-aspartic acid | + L-glutamic acid | − glycyl-L-asparatic acid | − glycyl-L-glutamic acid |
| v D-serine | + L-serine | + L-threonine | v D,L-carnitine | + γ-amino gutyric acid |
| − 2,3-butanediol | − glycerol | − D,L-α-glycerol phosphate | − glucose-1-phosphate | + glucose-6-phosphate |

As listed in the Table 3, the LG 31-3 strain was identified as *Burkholderia multivorans*. The inventors deposited the strain "*Burkholderia multivorans* LG 31-3" on Mar. 13, 2006 in the KCTC (Korean Collection for Type Cultures) of the KRIBB (Korea Research Institute of Bioscience and Biotechnology). The Deposition number was "KCTC 10920BP."

Example 4

Partial Purification of Amidase and Reaction of Crude Enzyme

The LG 31-3 strain was cultured in the same medium (5 ml) as in the Example 2, and then cultured in 1.5 of five flasks (150 rmp, 30° C.). When 50% of FAA was converted (cultured for 24 hours) during the culture, the culture solution was centrifuged to obtain 36.1 g (wet weight) of cell pellet, and the cell pellet was re-suspended in 200 in of 50 mM potassium phosphate buffer (buffer A, pH 7.2, 1 m MDTT, 1 mM EDTA included). The re-suspended cell solution was homogenized with a Bead beater (Biospec), and then centrifuged at a rotary speed of 5,000 rpm for 15 minutes to yield a supernatant from the crude enzyme solution.

Figure 2:
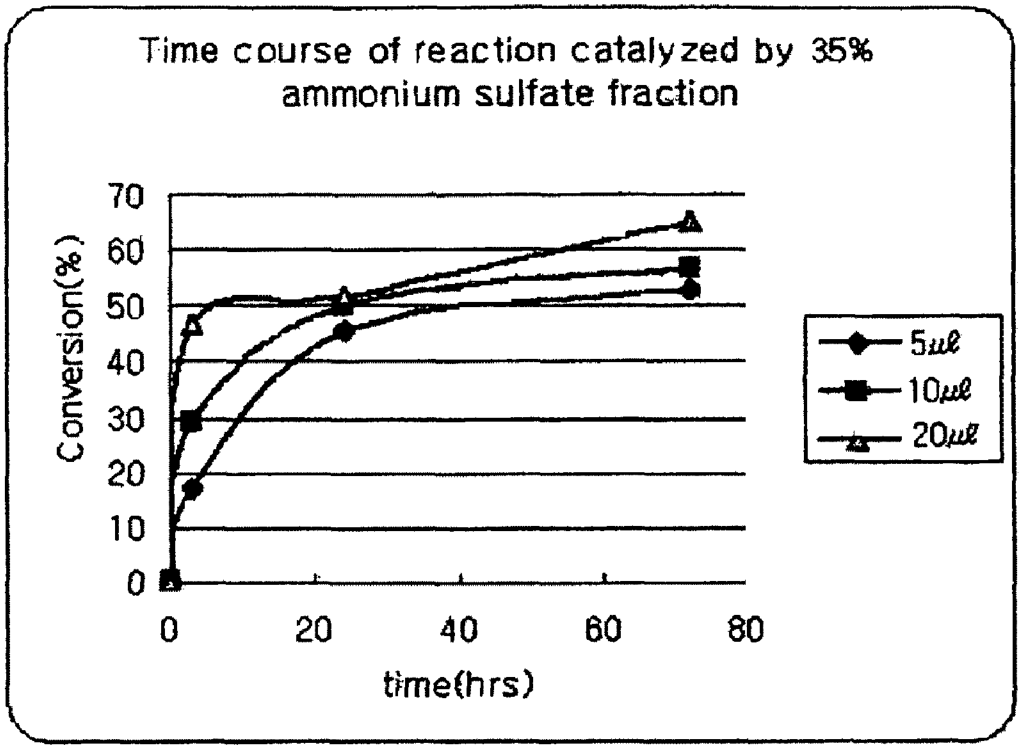
FIG. 2 is a graph showing a conversion ratio according to the passage of time in the hydrolysis of (R),(S)-2-(4-chlorophenyl)-3-methylbutyramide using amidase produced in the LG 31-3 strain according to the present invention.

Ammonium sulfate powder was added to the supernatant to prevent decomposition of the amidase by proteases present in the crude enzyme solution, and the resultant mixture was fractionated at saturation concentrations of 35, 55 and 75% under a constant temperature condition of 4° C. and dialyzed in a buffer solution (MWCO 12,000), and a concentration of proteins in the mixture was then measured using a Bradford method. Also, an ammonium sulfate precipitate solution, which was used as a crude enzyme solution, reacted with the substrate FAA. 10 μl of a FAA stock solution (422 mg/10 ml methanol) was added to different crude enzyme solutions, and then 50 mM Tris-HCl (pH 7.8) was added thereto to adjust the resultant mixture to the total amount of 1 ml, and then reacted with each other. 100 μl of test samples were taken from the culture mixture at different time points, and 50 μl of 1M $H_3PO_4$ was added to the test samples so as to stop the reaction, and 850 μl of acetonitrile was added thereto to perform a RP-HPLC analysis on the test samples (FIG. 2). As a results, the substrate was converted at a level of 35%, and an initial reaction rate was high when the crude enzyme solution was added at an increasing amount, as shown in FIG. 2. However, the reaction rate is significantly reduced if the conversion ratio is 50%, which indicates that the amidase according to the present invention has a stereoselectivity.

Example 5

Separation and Purification of Amidase

The 35% ammonium sulfate precipitate solution prepared in the Example 4 was desalted using PD-10 and concentrated using a YM10 membrane, and ion exchange chromatography (IEC) using Mono Q HR 5/5 was then carried out under the following conditions.

Conditions of Ion Exchange Chromatography (IEC)

Buffer A: 50 mM potassium phosphate (1 m MDTT, 1 mM EDTA included), pH7.2

Buffer B: 50 mM potassium phosphate (1 m MDTT, 1 mM EDTA included), 1M KCl, pH 7.2

Elution Conditions: 10 ml buffer A at the beginning, Linear gradient: 100% buffer B 50 ml After the ion exchange chromatography was carried out, hydrophobic interaction chromatography (HIC) using phenyl sepharose HR 5/5 was carried out 5 on 2.0 ml of test samples containing 1M ammonium sulfate under the following conditions.

Conditions of Hydrophobic Interaction Chromatography (HIC)

Buffer A: 50 mM potassium phosphate (1 m MDTT, 1 mM EDTA included), pH7.2, 1M ammonium sulfate Buffer B: 50 mM potassium phosphate (1 m MDTT, 1 mM EDTA included), pH 7.2

Elution Conditions: 20 min buffer A at the beginning, Linear gradient buffer B 72 ml 0.2 ml/min)

Figure 3A:
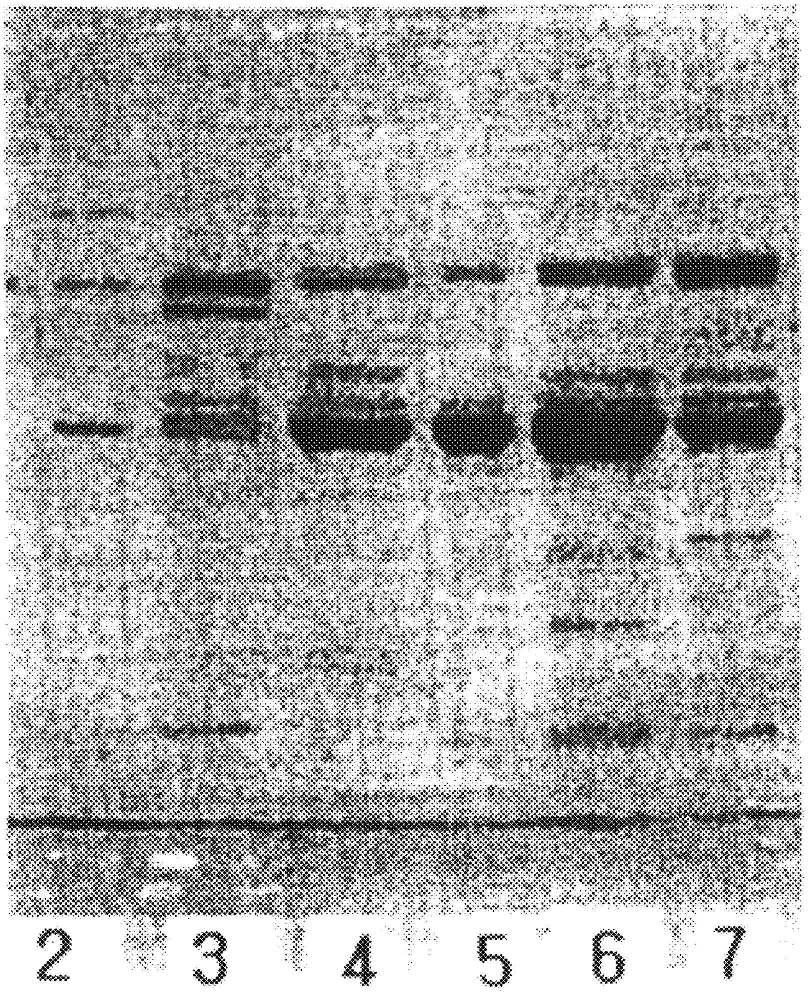
FIGS. 3*a* to 3*c* are photographs showing molecular weights of amidase measured on SDS-PAGE, the amidase being produced in an LG 31-3 strain of the present invention.
Figure 3B:
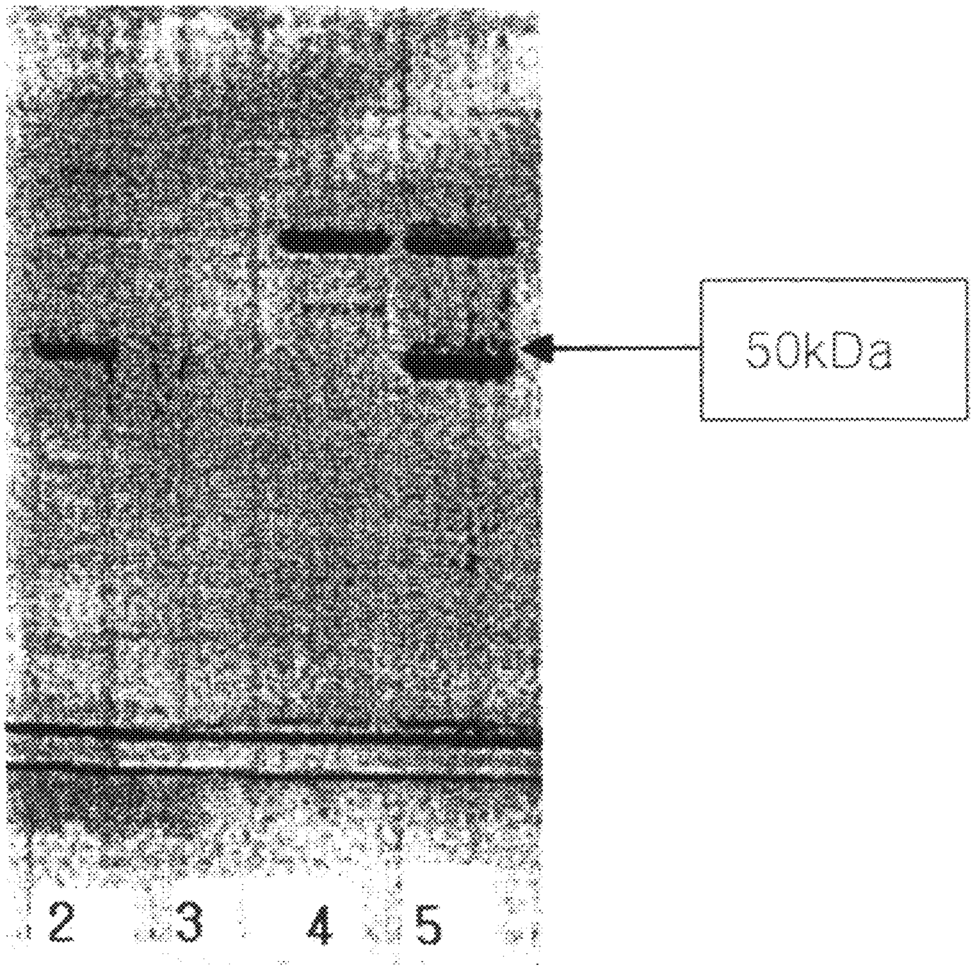

After the hydrophobic interaction chromatography was carried out, gel filtration chromatography (GFC) using Superose 12 HR 10/30 was carried out under the elution conditions: 50 mM potassium phosphate (1 m MDTT, 1 mM EDTA included, pH 8.0). FIGS. 3*a* and 3*b* show electrophoretic results of fractions on SDS-PAGE after the IEC and the GFC, respectively. As shown in FIGS. 3*a* and 3*b*, the native gel electrophoresis was carried out since pure proteins are not obtained even after the GFC.

Figure 3C:
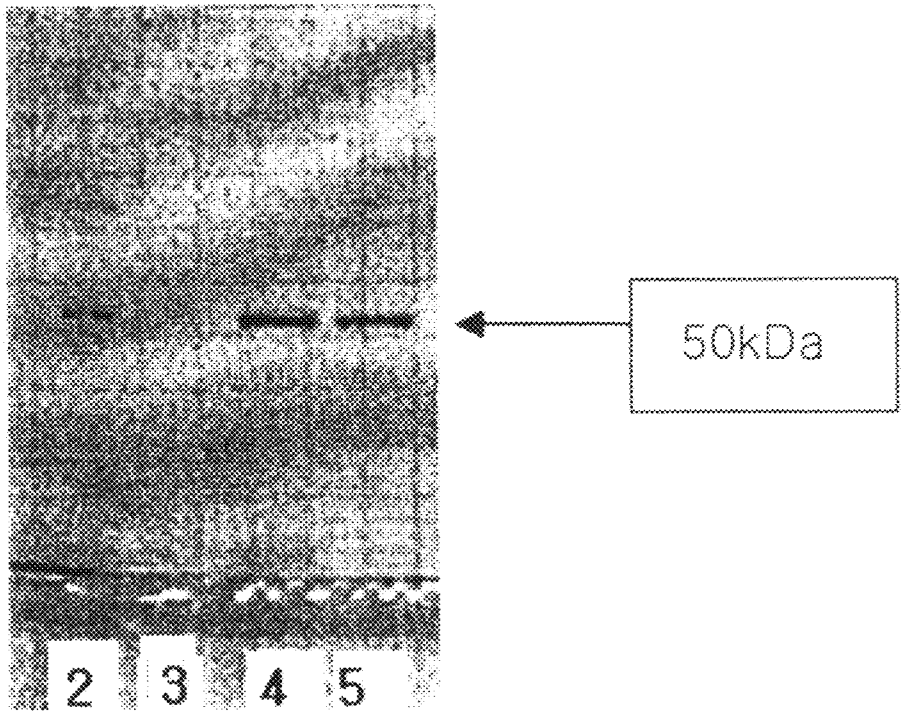

After the IEC was carried out, 84 μl of a dye solution was mixed with 16 μl of a fraction having an amidase activity, and the resultant mixture was developed in an SDS-free developer solution, cut by lane and stained, and regions with an observed band were cut out (7 bands), smashed into small pieces, and then stored at 5° C. for 3 days. 500 μl of 50 mM Tris-HCl (pH 7.8) was added to 500 μl of a supernatant, and 10 μl of an FAA stock solution was added thereto. SDS-PAGE (a denatured condition) on the bands 3 and 4, in which the reaction appears, was carried out to confirm that the amidase having a molecular weight of 50 kDa was purely isolated (FIG. 3*c*).

Example 6

Analysis of N-terminal and Internal Amino Acids

The test samples, obtained in the Example 5 after the GFC, were separated on SDS-PAGE, and then blotted on a PVDF membrane (CAPS buffer pH 11.0). The resulting test sample having a molecular weight of 50 kDa was analyzed for an N-terminal amino acid sequence.

Figure 4:
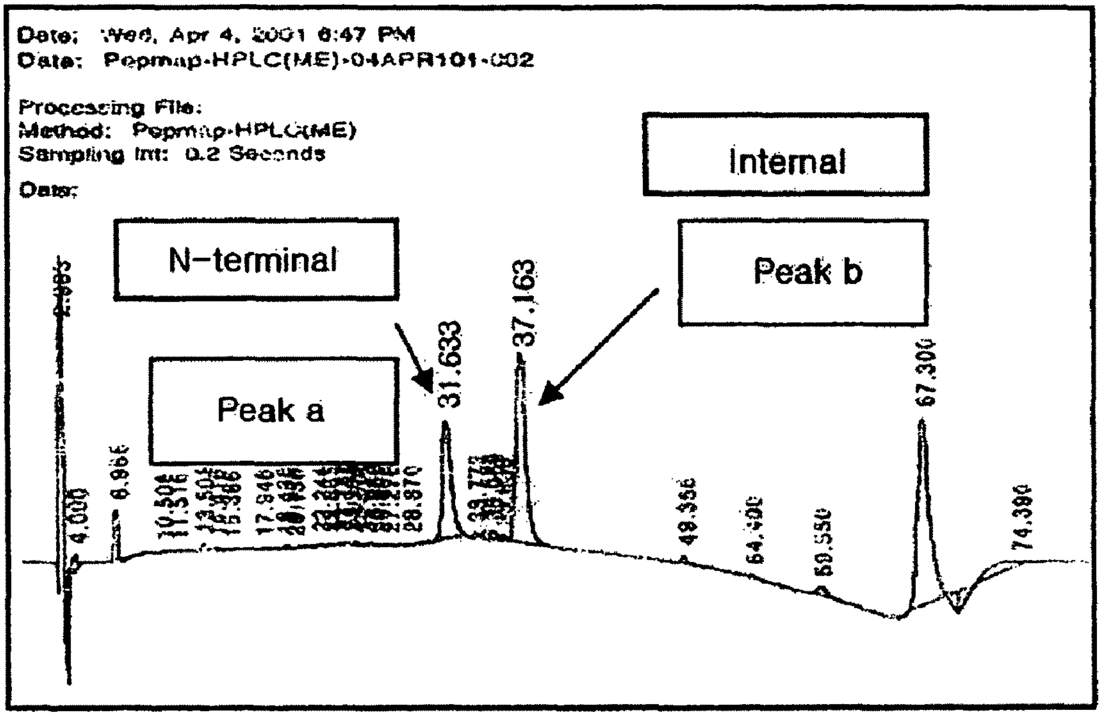
FIG. 4 is a chromatogram showing that the amidase produced in an LG 31-3 strain of the present invention is treated with trypsin, and the resultant peptides are then separated using reverse-phase HPLC.

In order to identify an inner sequence of the amidase, a fraction of the region having activity after the IEC was also treated with trypsin (Roche, modified for sequencing, for example a residue —COOH is substituted with lysine or arginine). 10 μl of a trypsin solution (concentration of 1 μg/μl, 50 mM potassium phosphate, 1 mM Mercaptoethanol, 1 mM EDTA included, pH 8.0) was mixed with 100 μl of the fraction having activity, and the resultant mixture was reacted at 37 for 4 hours. 50 μl of the resultant reaction solution was separated using RP-HPLC (1 ml/min, 210 nm, Capcell Pak 4.9×300 mm, Solvent Condition: Solvent A: 0.1% TFA water, Solvent B: 0.1% TFA acetonitrile, linear gradient 100% solvent B 60 min), and fractions eluted at 31.6 minutes and 37.2 minutes were concentrated, and their N-terminal amino acid analyses were then carried out (FIG. 4). As a result, the fraction eluted at 31.7 minutes has the same amino acid sequence as the N-terminal amino acid sequence blotted after the SDS-PAGE. The sequence is set forth in SEQ ID NO: 1, as follows. Also, the fraction eluted at 37.2 minutes has an amino acid sequence set forth in SEQ ID NO: 2.

```
[N-terminal amino acid sequence] SEQ ID NO: 1:
TTLGSLTLTEARHALRREF

[Internal amino acid sequence] SEQ ID NO: 2:
VTRPVRLALPRTTFWRGLAADVDALAQQA
```

INDUSTRIAL APPLICABILITY

As described above, the present invention provides a novel *Burkholderia multivorans* sp. LG 31-3 (KCTCX 10920BP), and an amidase having stereoselective substrate specificity, the amidase being produced in the strain. The amidase produced in the novel *Burkholderia multivorans* sp. LG 31-3 (KCTCX 10920BP) of the present invention can be useful to yield a single enantiomer (S)-2-(4-chlorophenyl)-3-methylbutyric acid at a high optical purity by easily optically resolving a racemic mixture (R),(S)-2-(4-chlorophenyl)-3-methylbutyramide under enzyme reaction conditions of room temperature and normal pressure.

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

What is claimed is:

1. A strain *Burkholderia multivorans* LG 31-3 (KCTC 10920BP) that produces amidase.

2. A method for producing an amidase, comprising:

culturing a strain *Burkholderia multivorans* LG 31-3 (KCTC 10920BP); and recovering amidase from the cultured strain, wherein said amidase has an internal amino acid sequence of SEQ ID NO:2.

3. An amidase produced according to the method of claim 2, and having an N-terminal amino acid sequence of SEQ ID NO: 1 and stereoselective substrate specificity.

* * * * *